(12) United States Patent
Yanik

(10) Patent No.: US 9,440,061 B2
(45) Date of Patent: Sep. 13, 2016

(54) INTRAVENOUS CONNECTION SITE PROTECTIVE DEVICE

(71) Applicant: John Yanik, Margate, FL (US)

(72) Inventor: John Yanik, Margate, FL (US)

(*) Notice: Subject to any disclaimer, the term of this patent is extended or adjusted under 35 U.S.C. 154(b) by 272 days.

(21) Appl. No.: 14/248,439

(22) Filed: Apr. 9, 2014

(65) Prior Publication Data

US 2015/0290449 A1    Oct. 15, 2015

(51) Int. Cl.
*A61M 39/10*    (2006.01)
*A61M 39/20*    (2006.01)

(52) U.S. Cl.
CPC .......... *A61M 39/1011* (2013.01); *A61M 39/20* (2013.01); *A61M 2039/1066* (2013.01)

(58) Field of Classification Search
CPC ........... A61M 39/1011; A61M 39/20; A61M 2039/1066; A61M 2039/1061; F16L 55/1141; F16L 55/13; F16L 55/136; F16L 55/1283; F16L 55/1612; F16L 55/11; H01R 13/443; H01R 13/44
USPC ................................................. 604/533–535
See application file for complete search history.

(56) References Cited

U.S. PATENT DOCUMENTS

| | | | |
|---|---|---|---|
| 4,473,369 A * | 9/1984 | Lueders | A61M 39/1011 285/419 |
| 4,730,435 A | 3/1988 | Riddle et al. | |
| 5,037,405 A * | 8/1991 | Crosby | A61M 39/1011 604/533 |
| 5,408,576 A | 4/1995 | Bishop | |
| 5,704,655 A * | 1/1998 | Lemburg | F16L 35/00 285/80 |
| D402,365 S | 12/1998 | Lubitz | |
| 6,035,102 A | 3/2000 | Bakke | |
| 7,031,602 B2 | 4/2006 | Faries, Jr. et al. | |
| D623,398 S | 9/2010 | Meiser et al. | |
| 2002/0036015 A1* | 3/2002 | Miyajima | F02M 25/0872 137/543.23 |
| 2009/0208277 A1* | 8/2009 | Werth | A61M 39/1011 403/312 |
| 2011/0084181 A1 | 4/2011 | Bowers et al. | |

FOREIGN PATENT DOCUMENTS

| | | |
|---|---|---|
| CN | 101002717 | 1/2013 |
| CN | 103316392 | 9/2013 |

* cited by examiner

*Primary Examiner* — Imani Hayman
*Assistant Examiner* — Hamza Darb

(57) ABSTRACT

An intravenous connection site protective device encloses an intravenous connection site and prevents tampering with and inadvertent separation of intravenous lines. The device includes an elongated sleeve having an interior space. Respective apertures extend through a first end and a second end of the sleeve. Each aperture receives an intravenous line therethrough. The interior space holds an intravenous line port coupled to a free end of one of the intravenous lines. A first section of the sleeve pivotally coupled to a second section providing access to the interior space. A closure secures the first section to the second section in a closed position wherein access to the interior space is inhibited by the sleeve.

7 Claims, 3 Drawing Sheets

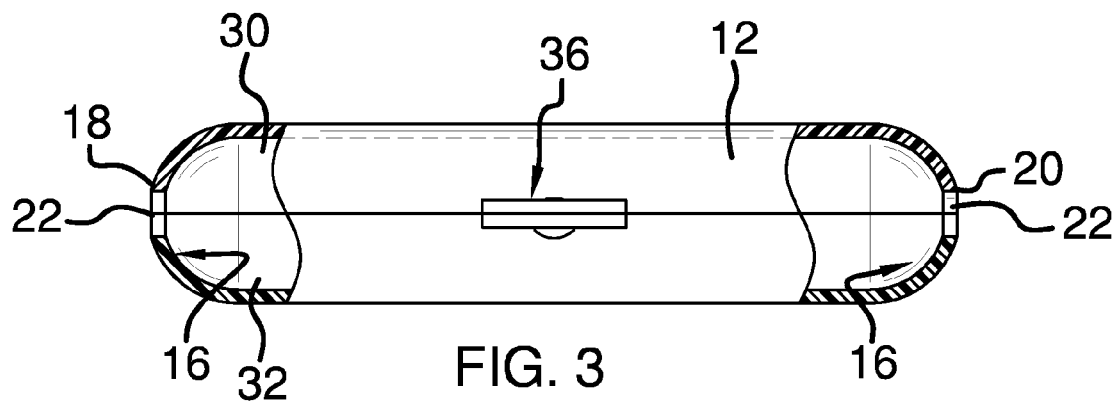
FIG. 3
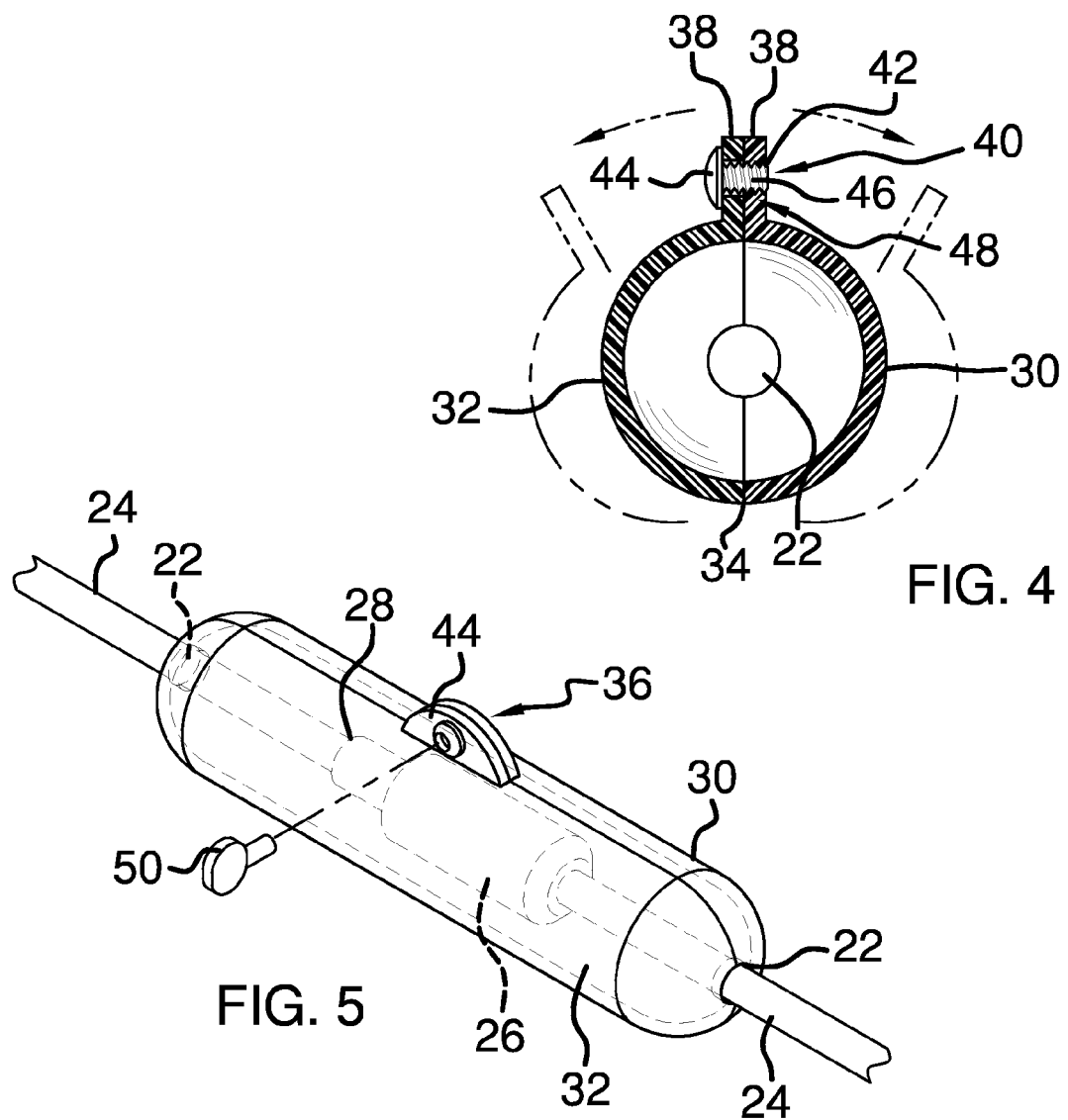
FIG. 4
FIG. 5

INTRAVENOUS CONNECTION SITE PROTECTIVE DEVICE

BACKGROUND OF THE DISCLOSURE

1. Field of the Disclosure

The disclosure relates to protective devices and more particularly pertains to a new protective device for enclosing an intravenous connection site and preventing tampering with and inadvertent separation of intravenous lines at an intravenous connection site.

2. Summary of the Disclosure

An embodiment of the disclosure meets the needs presented above by generally comprising an elongated sleeve having an interior space. Respective apertures extend through a first end and a second end of the sleeve. Each aperture receives an intravenous line therethrough. The interior space holds an intravenous line port coupled to a free end of one of the intravenous lines. A first section of the sleeve pivotally coupled to a second section providing access to the interior space. A closure secures the first section to the second section in a closed position wherein access to the interior space is inhibited by the sleeve.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 3 is a partial cut-away top view of an embodiment of the disclosure.

FIG. 4 is a cross-sectional view of an embodiment of the disclosure taken along line 4-4 of FIG. 1.

FIG. 5 is a top front side perspective view of an embodiment of the disclosure in use for a connected intravenous line.

DESCRIPTION OF THE PREFERRED EMBODIMENT

Figure 1:
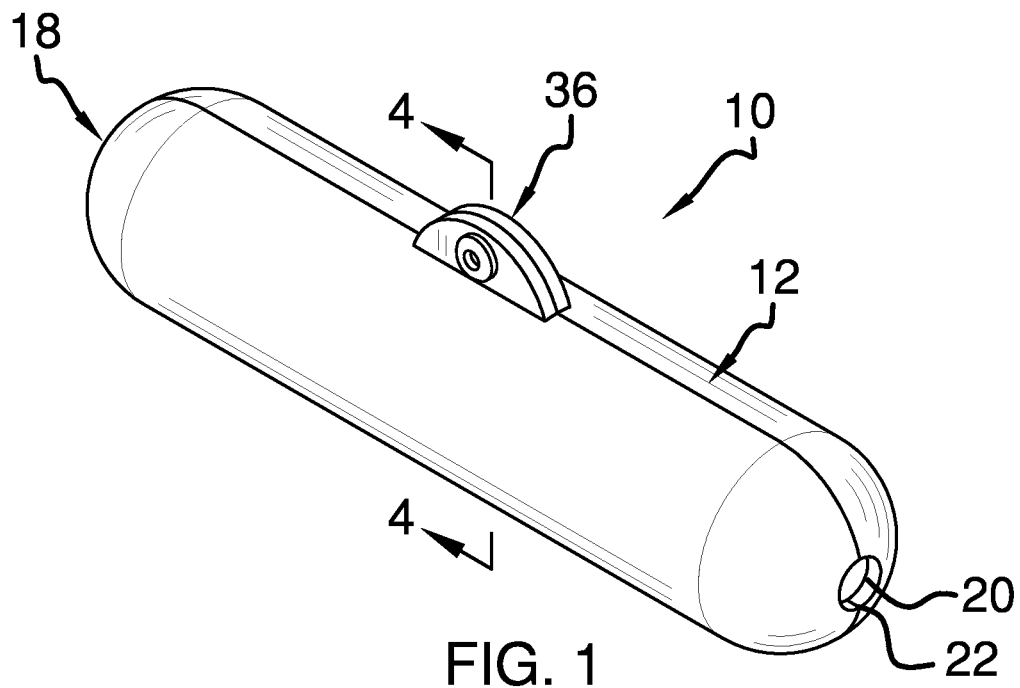
FIG. 1 is a top front side perspective view of an intravenous connection site protective device according to an embodiment of the disclosure.
Figure 2:
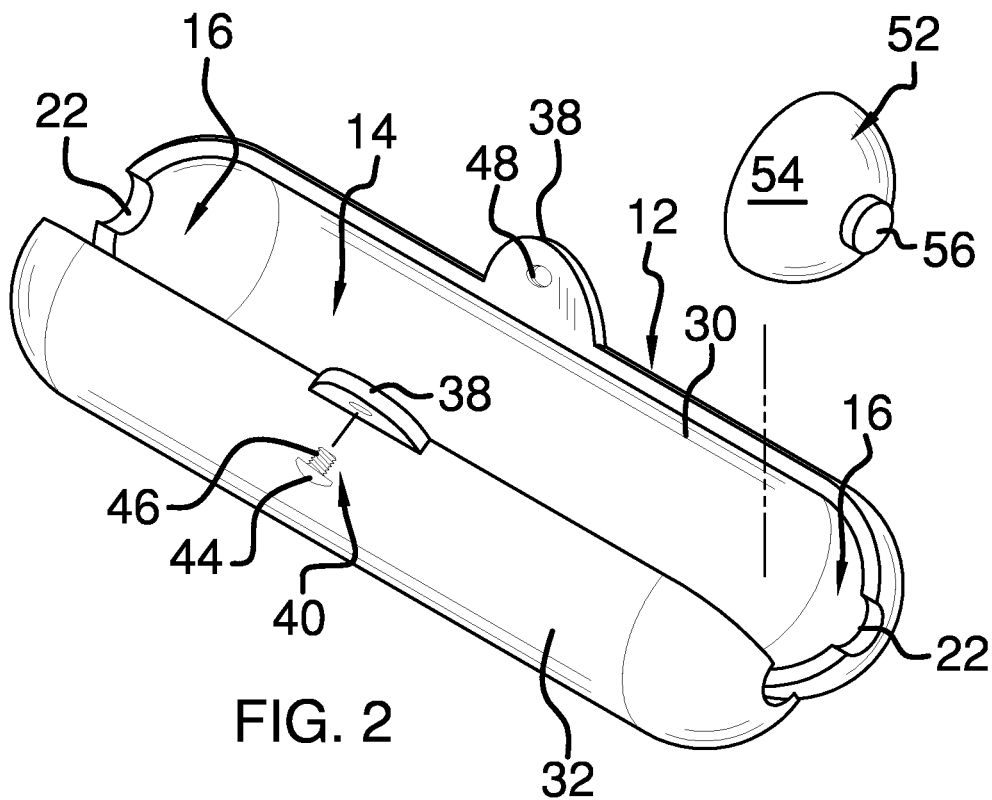
FIG. 2 is an exploded top front side perspective view of an embodiment of the disclosure.
Figure 6:
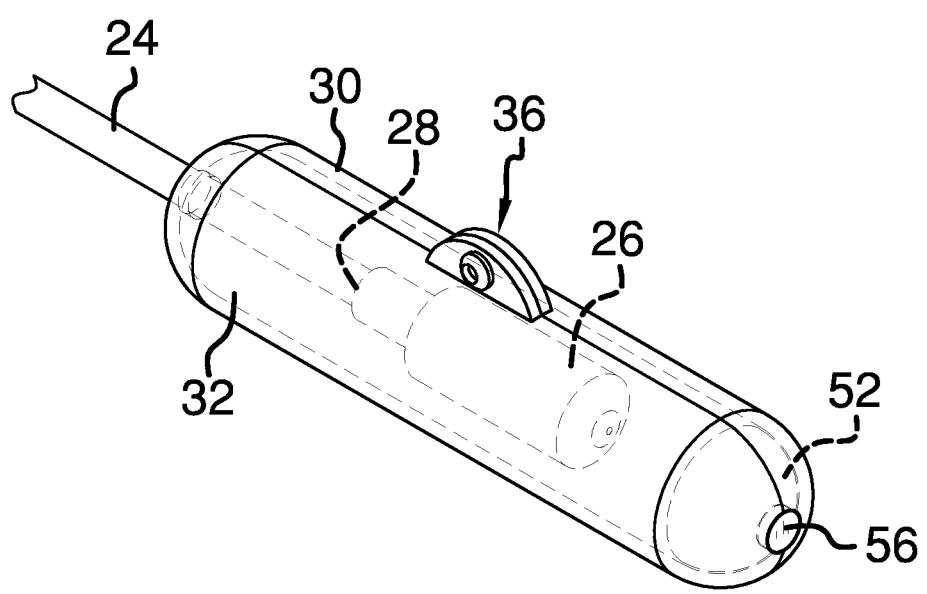
FIG. 6 is a top front side perspective view of an embodiment of the disclosure in use for an unconnected intravenous line.

With reference now to the drawings, and in particular to FIGS. 1 through 6 thereof, a new protective device embodying the principles and concepts of an embodiment of the disclosure and generally designated by the reference numeral 10 will be described.

As best illustrated in FIGS. 1 through 6, the intravenous connection site protective device 10 generally comprises a sleeve 12 having an interior space 14. Opposed ends 16 of the interior space 14 are concave. The sleeve 12 is elongated between a first end 18 and a second end 20. Respective apertures 22 extend through the first end 18 and the second end 20. Each aperture 22 is configured for receiving an intravenous line 24 therethrough. The interior space 14 is configured for holding an intravenous line port 26 coupled to a free end 28 of one of the intravenous lines 24. The sleeve 12 has a first section 30 pivotally coupled to a second section 32 wherein the sleeve 12 is openable providing access to the interior space 14. A living hinge 34 may couple the first section 30 to the second section 32.

A closure 36 is coupled to the sleeve 12. The closure 36 secures the first section 30 to the second section 32 wherein access to the interior space 14 is inhibited by the sleeve 12. The closure 36 comprises a pair of opposed panels 38 extending respectively from the first section 30 and the second section 32 and a fastener 40 couplable to the opposed panels 38 wherein the panels 38 are secured together preventing pivoting of the first section 30 relative to the second section 32. The fastener 40 may be a screw 42 having a head 44 and a threaded shaft 46. The threaded shaft 46 is extendable through the opposed panels 38 and engages threading 48 through at least one of the opposed panels 38, as shown in FIG. 4. Thus, the opposed panels 38 are secured together by the screw 42. A key 50 is engageable to the head 44 of the screw 42 wherein the screw 42 is rotatable by the key 50. The key 50 may uniquely correspond to the fastener 40 or screw 42 wherein disengagement of the fastener 40 from the panels 38 is substantially restricted to use of the key 50. This may be achieved in a conventional manner such as what is commonly used in other situations to inhibit vandalism or disengagement of fasteners used in areas accessible to the public.

A plug 52 is positionable in the interior space 14 such that the plug 52 obstructs one of the apertures 22 wherein the plug 52 is configured for protecting the intravenous line port 26. The plug 52 has a convex outer surface 54 complementary to the opposed ends 16 of the interior space 14. A nipple 56 extends from the plug 52. The nipple 56 is complementary to the one of the apertures 22 obstructed by the plug 52 wherein the nipple 56 is positionable in the one of the apertures 22 obstructed by the plug 52 holding the plug 52 adjacent to the one of the apertures 22 obstructed by the plug 52.

In use, the sleeve 12 is opened by pivoting the first section 30 and second section 32. The intravenous line port 26 is positioned in the interior space 14. The intravenous line port 26 coupled to the free end 28 of one of the intravenous lines 24 may be coupled to a second of the intravenous lines 24. The sleeve 12 is closed over the intravenous lines 24 and the closure 36 secured. Each aperture 22 has a diameter less than portions of the intravenous lines 24 within the interior space 14 such that the connection of the intravenous lines 24 is protected and cannot be uncoupled while the sleeve 12 is secured around the intravenous line port 26. Access to the intravenous line port 26 may be restricted and the intravenous line port 26 may be protected from contaminants by positioning the plug 52 within the interior space 14 when the intravenous line port 26 is not coupled to the second one of the intravenous lines 24.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An intravenous connection site protective device comprising:
   a sleeve having an interior space, said sleeve being elongated between a first end and a second end, respective apertures extending through said first end and said second end, each said aperture being configured for receiving an intravenous line therethrough, said interior space being configured for holding an intravenous line port coupled to a free end of one of the intravenous lines, said sleeve having a first section pivotally coupled to a second section wherein said sleeve is openable providing access to said interior space;
   a closure coupled to said sleeve, said closure securing said first section to said second section wherein access to said interior space is inhibited by said sleeve;
   a plug being positionable in said interior space such that said plug obstructs one of said apertures wherein said plug is configured for protecting the intravenous line port, said plug having a convex outer surface complementary to said opposed ends of said interior space; and
   a nipple extending from said outer surface of said plug, said nipple being complementary to said one of said apertures obstructed by said plug wherein said nipple is positionable in said one of said apertures obstructed by said plug holding said plug adjacent to said one of said apertures obstructed by said plug.

2. The device of claim 1, further comprising said closure comprising a pair of opposed panels extending respectively from said first section and said second section and a fastener couplable to said opposed panels wherein said panels are secured together preventing pivoting of said first section relative to said second section.

3. The device of claim 2, further comprising said fastener being a screw having a head and a threaded shaft, said threaded shaft being extendable through said opposed panels and engaging at least one of said opposed panels wherein said opposed panels are secured together by said screw.

4. The device of claim 3, further comprising a key, said key being engageable to said head of said fastener wherein said fastener is rotatable by said key.

5. The device of claim 4, further comprising said key uniquely corresponding to said fastener wherein disengagement of said fastener from said panels is substantially restricted to use of said key.

6. The device of claim 1, further comprising a living hinge coupling said first section to said second section.

7. An intravenous connection site protective device comprising:
   a sleeve having an interior space, opposed ends of said interior space being concave, said sleeve being elongated between a first end and a second end, respective apertures extending through said first end and said second end, each said aperture being configured for receiving an intravenous line therethrough, said interior space being configured for holding an intravenous line port coupled to a free end of one of the intravenous lines, said sleeve having a first section pivotally coupled to a second section wherein said sleeve is openable providing access to said interior space;
   a living hinge coupling said first section to said second section;
   a closure coupled to said sleeve, said closure securing said first section to said second section wherein access to said interior space is inhibited by said sleeve, said closure comprising a pair of opposed panels extending respectively from said first section and said second section and a fastener couplable to said opposed panels wherein said panels are secured together preventing pivoting of said first section relative to said second section, said fastener being a screw having a head and a threaded shaft, said threaded shaft being extendable through said opposed panels and engaging at least one of said opposed panels wherein said opposed panels are secured together by said screw;
   a key, said key being engageable to said head of said fastener wherein said fastener is rotatable by said key, said key uniquely corresponding to said fastener wherein disengagement of said fastener from said panels is substantially restricted to use of said key;
   a plug being positionable in said interior space such that said plug obstructs one of said apertures wherein said plug is configured for protecting the intravenous line port, said plug having a convex outer surface complementary to said opposed ends of said interior space; and
   a nipple extending from said plug, said nipple being complementary to said one of said apertures obstructed by said plug wherein said nipple is positionable in said one of said apertures obstructed by said plug holding said plug adjacent to said one of said apertures obstructed by said plug.

* * * * *